United States Patent [19]

Kotewicz et al.

[11] Patent Number: 5,017,492
[45] Date of Patent: May 21, 1991

[54] REVERSE TRANSCRIPTASE AND METHOD FOR ITS PRODUCTION

[75] Inventors: Michael L. Kotewicz, Columbia; James M. D'Alessio; Gary F. Gerard, both of Frederick, all of Md.

[73] Assignee: Life Technologies, Inc., Gaithersburg, Md.

[21] Appl. No.: 834,629

[22] Filed: Feb. 27, 1986

[51] Int. Cl.$^5$ .................. C12N 1/20; C12N 15/00
[52] U.S. Cl. ................. 435/252.3; 435/252.33; 435/320; 935/14; 935/72; 935/73
[58] Field of Search .......... 435/68, 172.3, 183, 435/194, 69.1, 71.1, 91, 252.3, 252.33, 320; 935/14, 23, 18, 29, 72, 73; 536/27

[56] References Cited

U.S. PATENT DOCUMENTS 4,663,290 5/1987 Weis et al. .................. 435/252.33
4,943,531 7/1990 Goff et al. .................. 435/194

FOREIGN PATENT DOCUMENTS

WO86/06741 11/1986 World Int. Prop. O. ...... 435/172.3

OTHER PUBLICATIONS

Kotewicz, M. L. et al., *Gene* 35:249-258 (1985).
Tanese, N. et al., *P.N.A.S.* (U.S.A.) 82:4944–4948 (1985).
Roth, M. J. et al., *J. Biol. Chem.* 260:9326-9335 (1985).
Lai, M. H. T. et al., *J. Virol.* 27:823-825 (1978).
Moelling, K. et al., *J. Virol.* 32:370-378 (1979).
Lai, M. H. T. et al., *J. Virol.* 25:652-663 (1978).
Gerard, G. F., *J. Virol.* 26:16-28 (1978).
Tronick, S. R. et al., *Proc. Nat'l. Acad. Sci.* (U.S.A.) 76:6314-6318 (1979).
Gerard, G. F. et al., *J. Virol.* 15:785-797 (1975).
Gerard, G. F. et al., *Biochemistry* 13:1632-1641 (1974).
Shinnick, T. M. et al., *Nature* 293:543-548 (1981).
Benard, H. V. et al., *Meth. Enzym.* 68:482-492 (1979).
Remault, E. et al., *Gene* 15:81-93 (1981).
Rosenberg, M. et al., *Meth. Enzym.* 101C:123-138 (1983).
Chung, C. H. et al., *Proc. Natl. Acad. Sci* (U.S.A.) 78:4931-4935 (1981).
Waxman, L. et al., *J. Biol Chem.* 260:12022-12028 (1985).
Goldberg, A. L. et al., *J. Biol. Chem.* 260:12029-12034 (1985).

*Primary Examiner*—James Martinell
*Attorney, Agent, or Firm*—Sterne, Kessler Goldstein & Fox

[57] ABSTRACT

The cloning of truncated versions of Moloney murine leukemia virus reverse transcriptase enzyme in *E. coli* is disclosed. The truncated reverse transcriptase enzymes have improved half-life when compared to native reverse transcriptase.

5 Claims, 9 Drawing Sheets

REVERSE TRANSCRIPTASE AND METHOD FOR ITS PRODUCTION

BACKGROUND AND OBJECTS OF THE INVENTION

This invention relates to the application of recombinant DNA procedures to the production of useful enzymes. More specifically, it relates to the cloning and expression of a reverse transcriptase from a new source, Moloney murine leukemia virus, and to methods for the large-scale preparation of the enzyme so cloned.

The RNA tumor viruses cause the integration into host cell DNA of genetic material coding for the production of several proteins. Among these are the reverse transcriptase (hereinafter RT) enzymes, which direct the synthesis of complementary DNA from an RNA template. One member of this family of enzymes has been found to have great utility, and has been widely used.

Avian myeloblastosis virus (AMV) RT has been an essential tool in recombinant DNA technology. During the course of its use, numerous studies have been performed attempting to establish conditions optimal for the synthesis of full-length complementary DNA in high yield from mRNA (see Berger, S.L., et al., Reverse transcriptase and its associated ribonuclease H: interplay of two enyzmatic activities controls the yield of single-stranded complementary deoxyribonucleic acid. Biochemistry 22 (1983) 2365-2372.) Recent evidence indicates that nucleolytic activities that are an integral part of the enzyme (i.e., RNase H or DNA endonuclease; Gerard, G.F.: Reverse transcriptase in Jacob, S.T. (Ed.), Enzymes of Nucleic Acid Synthesis and Modification, Vol. I, DNA Enzymes. CRC Press, Boca Raton, FL, 1983, pp. 1-38.) or associated contaminants have strikingly adverse effects upon the length and yield of complementary DNA during synthesis (Berger et al., 1983).

Cloning and over-expression of the enzyme in E. coli should afford the opportunity to engineer and purify a form of RT more suitable for applications in recombinant DNA technology. However, there are apparent obstacles to expressing AMV RT in bacteria. In particular, to generate native AMV RT, the avian polymerase gene product must form a dimer that is phosphorylated and cleaved proteolytically at a specific site in one subunit, events that are not catalyzed in E. coli.

Accordingly, it is an object of the present invention to provide an improved form of reverse transcriptase, and genetic material coding therefor, which is suitable for use in recombinant DNA technology.

A further object of the invention is to provide improved means for the expression of the RT genetic material.

Yet another object of the invention is to provide improved means for the purification of the RT enzyme so expressed.

SUMMARY OF THE INVENTION

The inventors herein noted that the Moloney murine leukemia virus (hereinafter M-MLV), produces a reverse transcriptase which is smaller than the avian RT (80 kDal), is monomeric, may not be phosphorylated and would not necessarily have to be cleaved proteolytically during its biosynthesis. Moreover, the nucleotide sequence of the M-MLV genome is known and the amino- and carboxyterminal amino acid sequences of M-MLV RT have been established. It therefore appeared that the M-MLV enzyme might be more suitable for cloning and expression than AMV RT, provided, however, that the cloned form of M-MLV RT had the desired activity.

This has proven to be the case. Broadly stated, the present practice of the invention, which involves several newly developed techniques, is as follows:

An expression vector is constructed containing the strong leftward promoter ($p_L$) of bacteriophage $\lambda$, the ribosome-binding site (RBS) of the cII gene of $\lambda$, and a unique downstream Nde I restriction site for construction of an ATG initiation codon. The Nde I site (CATATG) contains an ATG codon, so when it is cut and filled in with Pol IK (Klenow), any fragment with TG at its 5' end which is ligated to it will reconstruct both the site and the initiation codon. An appropriate TG sequence exists at the 5' end of the M-MLV RT coding sequence. Another plasmid is constructed which contains M-MLV proviral DNA and an upstream Eco R I site. This site is cut with Eco R I and digested with Bal-31 nuclease. After the digestion products are blunt-end ligated to the cut and blunted Nde I site of the expression vector, the resultant plasmids are screened for Nde I site reconstruction and the desired in-frame ATG. This method of reconstructing the ATG codon is another novel aspect of the invention.

A terminator source is constructed separately containing a universal terminator sequence.

A series of plasmids is then created by ligating a fragment of the terminator source, containing the universal terminator sequence, with a series of fragments of the expression vector which have had the 3' ends of their RT coding regions removed to varying extents by Bal-31 nuclease. The resultant plasmids have deletions of varying numbers of base pairs, depending on the time length of Bal-31 nuclease digestion, followed by the universal terminator sequence. This method for placing a translation termination codon at any of various locations near the 3' end of the cloned RT gene is yet another important aspect of the invention.

With the pRT300 and pRT600 series plasmids thus created, the analogous series of RTs may be used to study the influence of the carboxy-terminus structure on the RT activity level in E. coli. It has been found that the variation in enzyme activities is principally caused by differing stabilities of the enzymes in E. coli.

One particular member of the pRT600 series, pRT601, used with the host E. coli strain N4830, is used for large-scale production of the M-MLV RT. A further feature of this invention is the method for purifying the enzyme from the large volume of medium which is needed to extract it from the cells. According to this method, the RT is precipitated with ammonium sulfate and re-solubilized, then further isolated by successive chromatographic adsorptions in the presence of non-ionic detergents; the process is described more fully below.

DESCRIPTION OF THE FIGURES AND OF THE PREFERRED EMBODIMENTS OF THE INVENTION

BRIEF DESCRIPTION OF THE DRAWINGS

A preferred practice of the invention, as exemplified by the Examples to be set forth hereunder, is illustrated by the Figures, in which.

As shown in FIG. 1, phage λ control sequences and pBR322 plasmid DNA (Bernard, H.U. and Helinski, D.R.: Use of the λ phage promoter $p_L$ to promote gene expression in hybrid plasmid cloning vehicles. Methods Enzymol. 68 (1979) 482–492; Remaut, E., et al.: Plasmid vectors for high-efficiency expression controlled by the $p_L$ promoter of coliphage lambda. Gene 15 (1981) 81–93; Rosenberg, M., et al: The use of pKC30 and its derivatives for controlled expression of genes. Methods Enzymol 101C (1983) 123–138) are used to construct a cloning vehicle ("expression vector") for expression of the murine RT gene in *E. coli*. To avoid the frequently used strategy of fusing a eukaryotic gene to an N-terminal coding region of a bacterial gene, which would generate a fusion protein that might be altered in its biochemical properties, an Nde I site is placed immediately downstream from the λ control sequences for introduction of an ATG initiation codon at the 5′ end of the RT coding sequence. The examples to follow describe the presently preferred expression vector, plasmid pKD1, and its construction in more detail.

Figure 1A:
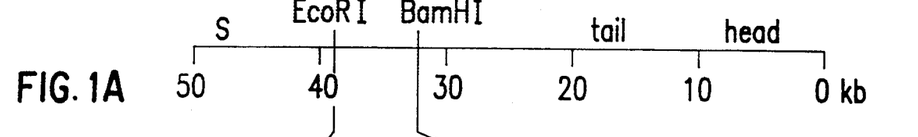
FIGS. 1A through 1C are gene map diagrams of the bacteriophage λ showing the locations of genes, promoters, and restriction sites relevant hereto.
Figure 1B:
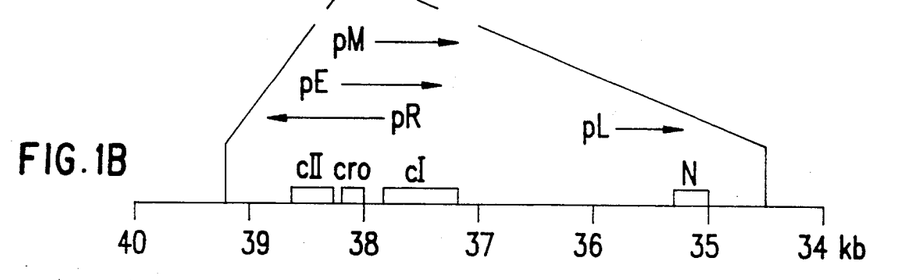
Figure 1C:
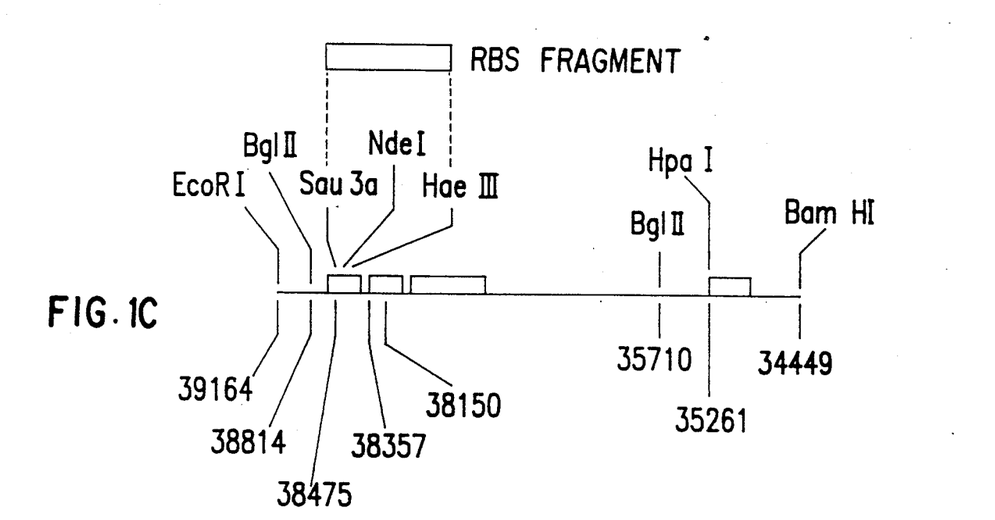
Figure 1D:
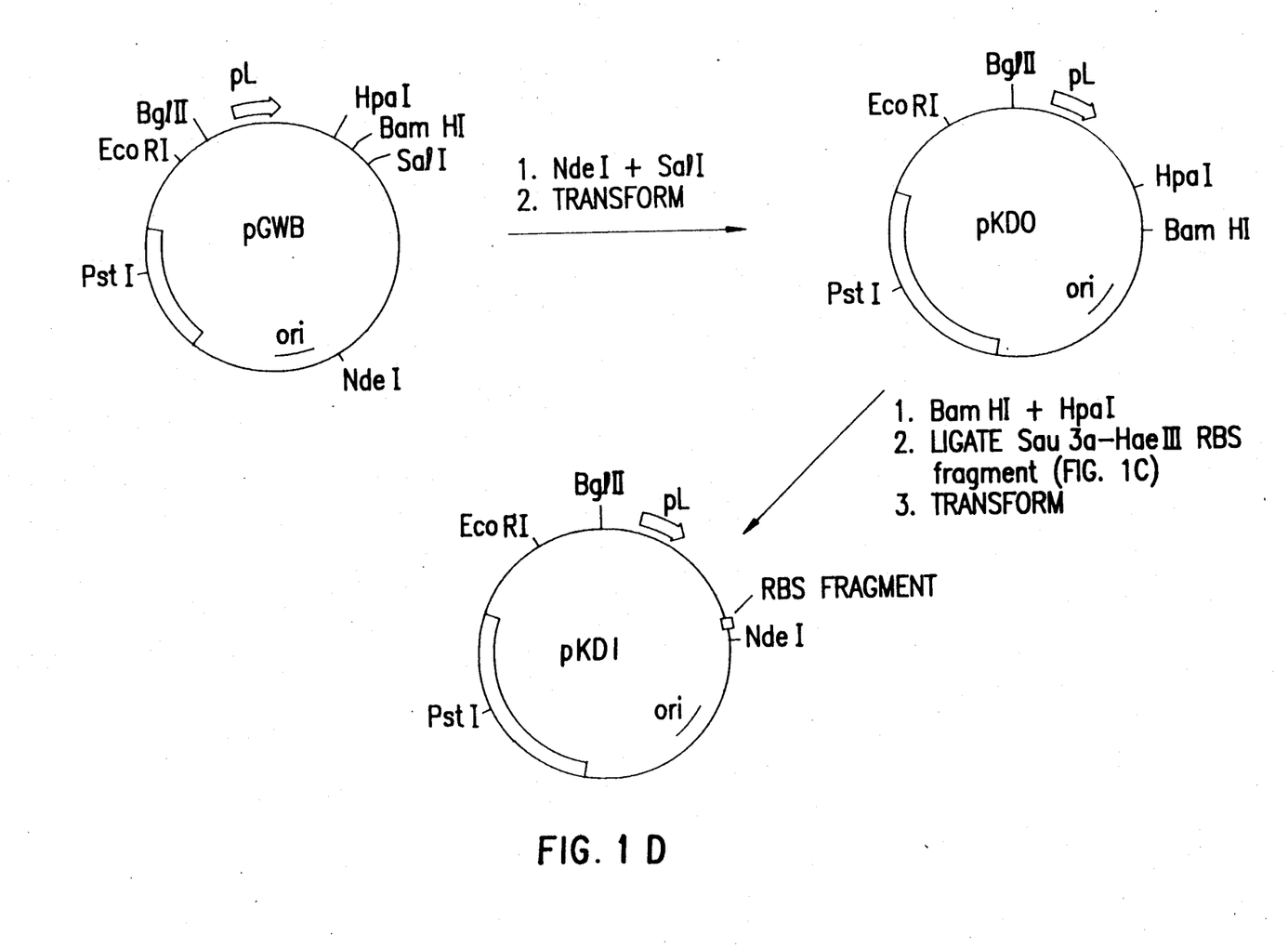
FIG. 1D is a schematic illustration showing the preparation of a preferred expression vector, pKD1.
Figure 2A:
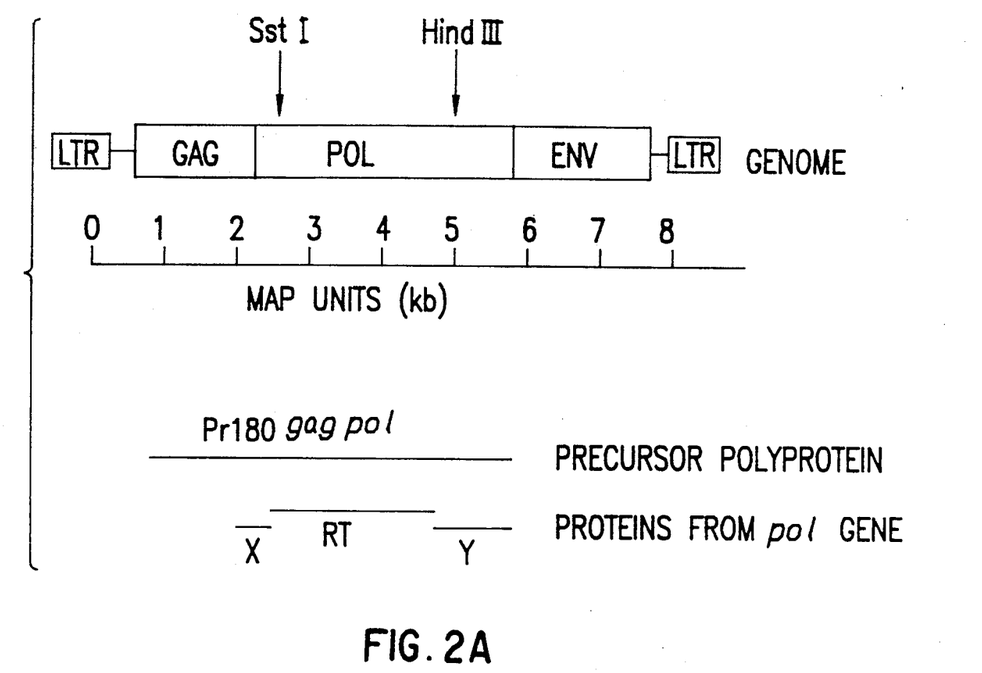
FIG. 2 is a gene map diagram of M-MLV showing the location of the desired RT gene, and in more detail, the base pair sequences at its ends.

It then remains to insert the RT coding material in such a manner that proper translation may occur. Mature M-MLV RT is generated in virus-infected cells by post-translational proteolytic processing from an internal region of a larger polyprotein precursor [see Gerard (1983) for review and FIG. 2A]. Elimination of DNA sequences flanking the RT-coding region in M-MLV DNA is desirable to bring the ends of this region juxtaposed to translation initiation and termination codons.

First (see FIG. 3), a plasmid or equivalent gene source is constructed which contains an Eco-RI site just upstream from the RT-coding region of M-MLV DNA. In the presently preferred embodiment, plasmid pRT1 is used.

When the Nde I recognition sequence in the expression vector is cut and filled in with PolIK (*E. coli* DNA polymerase I, Klenow fragment), the following terminal sequence is created downstream of $p_L$

5′ ... CATA
3′ ... GTAT

The last A is the first base of the initiation codon (ATG) for the now missing cII gene. When any DNA fragment ending in

Figure 2B:
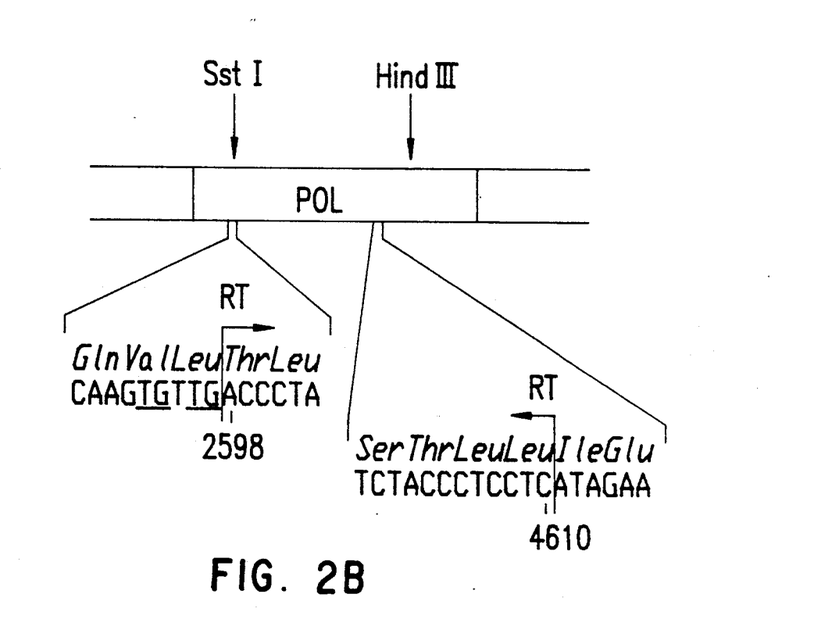

5′-TG...
3′-AC...

is blunt end ligated to this sequence the Nde I recognition site is reconstructed, and a translation initiation codon is created. Several in-frame TG pairs flanking the 5′ end of the M-MLV RT coding region may be used to reconstruct the Nde I site, including one immediately adjacent to the ACC triplet that codes for the N-terminal threonine of M-MLV RT (FIG. 2B). Therefore, a population of BAL 31-digested inserts is cloned into the filled-in Nde I site of the expression vector. The resulting set of plasmids is screened for the presence of an Nde I site. Insertion of DNA containing a particular gene will generate fusions both in and out of the 'correct' translation reading frame starting with the ATG contained in the Nde I site. Those in the 'correct' frame can code for a protein with additional or missing amino acids. Further screening is therefore necessary to choose the insert with the desired in-frame ATG. This procedure yielded plasmid pRT210, the preliminary vector of the preferred embodiment. Its Nde I site is reconstructed at position 2596 of the M-MLV genome (see FIG. 2B), just upstream of the initial threonine codon of RT.

Figure 4:
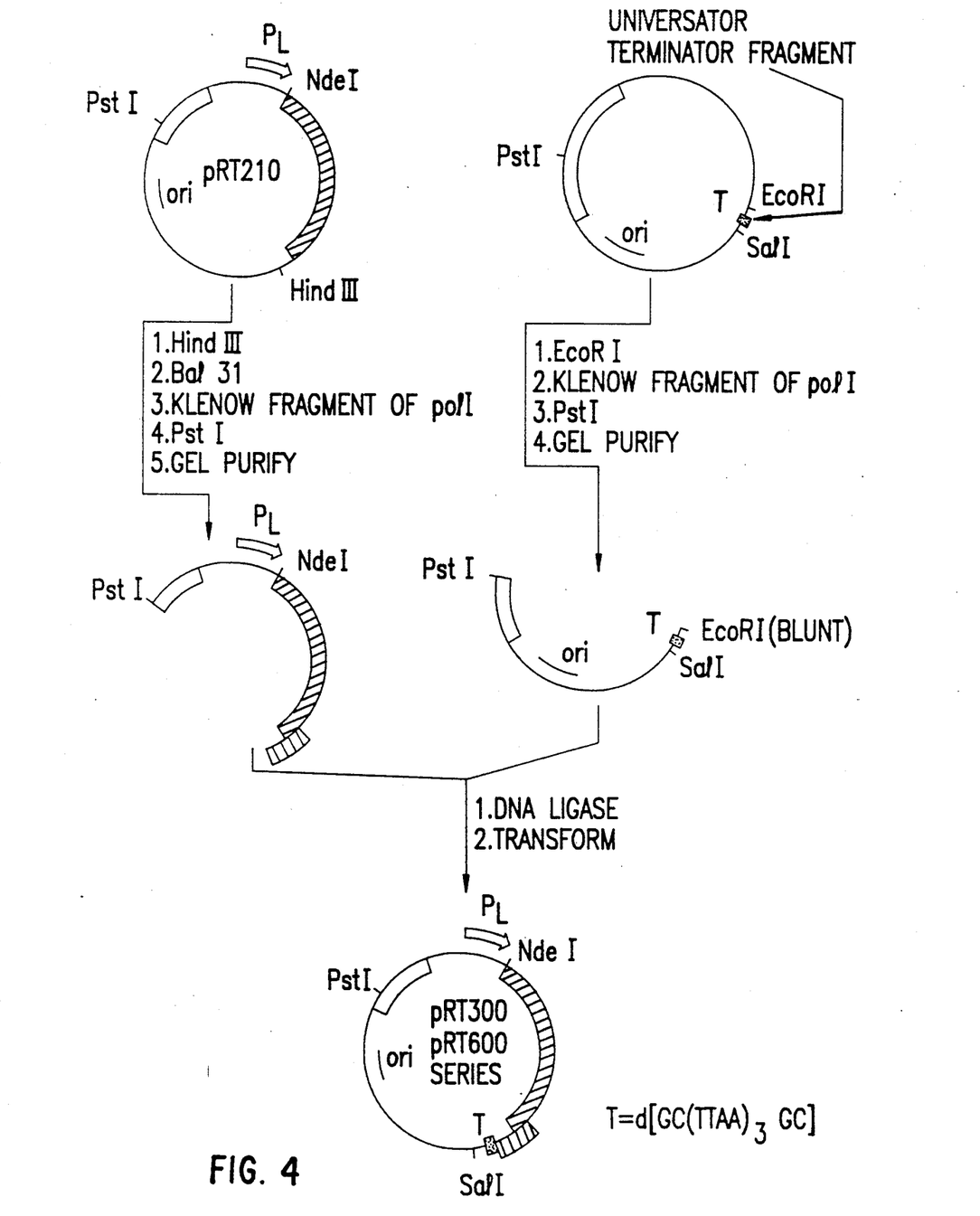
FIG. 4 is a schematic illustration showing the preparation of the preferred RT vectors of the invention, the pRT300 series and pRT600 series, from pRT210.

It is also necessary to introduce a termination control sequence at the 3′ end of the RT. The inventors (Kotewicz, M.L., et al., (1985). Cloning and overexpression of Moloney murine leukemia virus reverse transcriptase in *Escherichia coli*. Gene 35, 249–258) constructed plasmid pRT103, derived from pRT210, in an attempt to meet this need. A 643 bp fragment (including 57 bp from the RT region) was deleted from the vicinity of the 3′ end; an in-frame termination codon was present 172 bp downstream from the new junction. The RT protein synthezized thus had the 19 carboxy-terminal amino acids of the native protein replaced by 57 amino acids derived from the pBR322 tet sequence read out of frame. The RT was expressed in *E. coli* 2077 (λ), but the level of activity and stability were lower than desired. An alternate technique (see FIG. 4), which has become the preferred method, was then designed for inserting a translation termination codon at a number of locations near the 3′ end of the RT coding region:

A series of plasmids is created by ligating a fragment of pBRT, containing a unique Sal I site and a universal terminator sequence just inside a blunted EcoR I site, with a series of fragments of pRT210. Those fragments contain the expression and coding regions for the M-MLV RT, except that the 3′ ends of the RT coding regions have been removed to varying extents by Bal-31 nuclease. The resultant plasmids have average deletions of about 200 to 400 base pairs, depending on the time length of Bal-31 nuclease digestion, followed by the universal terminator sequence.

It will be clear to one skilled in the art that useful expression vectors (that is, plasmids with the $p_L$ promoter, the RBS and a unique Nde I site correctly spaced) may be created from λ and other host plasmids than pBR322. It will of course be desirable to remove any other Nde I sites from the host plasmid before insertion of the RBS and Nde I site-containing fragment, to facilitate screening for the proper enzyme coding insertion.

The utility of the preferred expression vector is due to the fact that in λ, there is an Nde I site containing an ATG codon at the correct spacing from the RBS.

There may be other sources of gene expression material wherein ATG codons are spaced appropriately (generally 8 bp) from an RBS in a site for a different restriction enzyme, e.g. Nco I, etc. The applicability by one skilled in the art of this method, that is, the reconstruction of an in-frame ATG codon at or near the exact 5' end of a desired coding sequence to be inserted, is thus seen to be broad, especially in view of the existence of an ATG codon at the beginning of most genes in cellular genomes.

We have found (see Example 7, below) that the amino acid sequence within 50 amino acids of the carboxy terminus of cloned M-MLV RT has a dramatic influence on the stability of RT in E. coli. A change of only three amino acids near the end of RT can cause a 7-fold change in its half life. These results are difficult to interpret in light of the paucity of detailed information available on the mechanisms of protein degradation in E. coli. For example, the half life of RT coded by pRT608 or 306 was increased by a factor of two in lon$^-$ cells, although the half lives of most of the RT's were unchanged in lon$^-$ mutants. It may be that the carboxy ends of RT from pRT608 and 307 contain a recognition site for protease La, coded by the lon gene. However, this conclusion must be considered tentative.

In an attempt to make some correlation between the structure of the carboxy terminus of RT and its stability in E. coli, the method of Garnier (Garnier, J., et al. (1978). Analysis of the accuracy and implications of simple methods for predicting the secondary structure of globular proteins. J. Mol. Biol. 120, 97–120) can be used to predict the secondary structures of the carboxy termini of the various RT constructs. (FIG. 6B) The RT constructs disclosed herein can be divided into two groups, less stable ($t1/2=2-7$ min) and more stable ($t1/2=26-35$ min). A single ordered secondary structural feature is found to be unique to the more stable RTs. This is the presence of an α-helix containing 18 amino acids adjacent to the carboxy end of the protein. The less stable RTs had α-helices in a comparable position at the end of the protein, but these contained a smaller or greater number of amino acids. One may speculate that only RTs with a buried carboxy terminus are stable in E. coli. Perhaps an α-helix of 18 amino acids can be uniquely accommodated within a groove of the RT tertiary structure; an α-helix containing less than or greater than 18 residues might not be buried and therefore exposed to proteolytic attack.

It appears that alteration of the carboxy terminal structure of authentic M-MLV RT by the removal of as many as 62 or the addition of as many as 43 amino acids does not significantly alter the DNA polymerase activity of purified RT. This is consistent with data indicating that the DNA polymerase and RNase H catalytic site(s) of RT is located within 250 amino acids of the RT amino terminus. The model in FIG. 6A of the secondary structure of M-MLV RT contains several potential super-secondary structures in this region that are necessary for these enzymatic activities: two polypeptide double helices composed of an anti-parallel sequential ββ dimer that could be involved in DNA binding (residues 77–92, 97–115); and a potential βαβαβ nucleotide fold that could be involved in nucleotide binding (residues 144–189).

A relatively large volume of buffered aqueous media is required to efficiently extract cloned M-MLV RT from E. coli cells (10 ml per gram of cells), which results in the generation of volumes of extract which become unworkable when kilogram quantities of cells are used. In the method herein to be described, M-MLV RT is concentrated from these large volumes by precipitation with $(NH_4)_2SO_4$. A key step in the method of the invention is the method used to solubilize the M-MLV RT from the $(NH_4)_2SO_4$ precipitate.

In order to conveniently obtain from large quantities of starting material the substantially pure enzyme of the invention which is soluble and stable during storage at $-10°$ to $-30°$ C., is essentially free of contaminating nuclease and other interfering activities, and is capable of catalyzing full-length cDNA synthesis from mRNA of any length primed with oligo (dT)$>10$, a number of steps are preferably carried out, in the sequence noted. The method of the invention is designed to isolate the enzyme by sequentially removing nucleic acids, low molecular weight metabolic intermediates and lipids, and proteinaceous impurities in a sequence which will preserve the enzyme in a soluble and stable form. The pure enzyme of the invention is substantially free of contaminating ribonuclease activities associated with virion-derived avian and murine RTs purified by prior art which interfer with the synthesis of full-length cDNA copies of RNA. By following the method of the invention to be described, there is produced a novel and theretofore unavailable enzyme in milligram quantities.

The starting material for the practice of this invention is E. coli strain N4830 bearing the plasmid pRT601 which contains the gene for M-MLV RT downstream of the phage λ pL promoter and cII ribosome binding site in a pBR322 derived plasmid, as discussed above. E. coli strain N4830, described in prior art, (Gottesman, M.E., et al; Transcription Anti-Termination by Bacteriophage Lambda N Gene Product. J. Mol. Biol. Vol. 140 (1980) pp 57–75.) was derived by lysogenizing E. coli strain SA 1615 with lambda xisl. In a complex set of selections most of the prophage was deleted including phage recombination genes, phage head and tail structural genes, lysis genes and the phage cro repressor gene. Virtually all of the lambda genome is deleted except for the cI repressor gene and the antitermination gene N. This strain carries the temperature sensitive cI allele cI indlts 857.

Frozen cells are thawed and a uniform suspension is made in an aqueous medium buffered to about pH 8.0 by the presence therein of Tris-HCl in a concentration of about 10 to 50 mM (optimally of 20 mM). The pH can vary in the range of about 7.3 to 8.4 which we will call mildly alkaline. Those skilled in the art will know that the actual working range will depend somewhat on experimental conditions but must be such that the protein is protected and has the proper adsorbency characteristics. A suitable reducing agent should be present in the medium. Such a reducing agent is dithiothreitol present in the medium at a concentration of from about 0.5 to 5 mM, optimally at 1.0 mM; others such as α-mercaptolethanol, will be known to those skilled in the art. It is preferred to include in the medium a chelator for heavy metals which deleteriously affect the active enzyme. A suitable such chelator is ethylenediamine - tetracetic acid (EDTA), present therein in a concentration of from about 0.1 to 2 mM, optimally 1 mM. It is also preferred to include a suitable inhibitor of proteolytic enzyme activity in order to preserve the stability of the enzyme. One such protease inhibitor is phenylmethylsulfonyl fluoride (PMSF), present in the medium at a concentration of from about 0.1 to 1 mM, optimally 0.2 mM. The medium must also contain an inert, soluble salt in order to preserve the enzyme in a soluble and active form. A suitable salt is NaCl, present in the medium at a concentration of from about 0.05 M to 0.15 M, optimally for extraction at 0.025 M. Where we have used NaCl in the various aqueous media, other monovalent salts such as KCl, NH$_4$Cl may usually be employed. After removal of nucleic acids, the optimum is 0.1 M. To the suspension is added a freshly prepared solution of lysozyme, preferably at about 13 mg/ml (0.1 ml of lysozyme/gm of starting cells) to digest cell walls. After thorough mixing, the suspension is allowed to stand for 20 minutes with occasional stirring.

To the spheroplasts generated by treatment with lysozyme is added a 10% (w/v) solution of sodium deoxycholate (0.5 ml of 10% sodium deoxycholate/gm of starting cells) to lyse the spheroplasts. After thorough mixing, the suspension is allowed to stand for 20 minutes with occasional stirring. The suspension at this point is a thick, gelatinous mass due to cell lysis and the release of DNA and associated protein from the cells.

Before proceeding with chromatographic fractionation of RT, extracts are treated to reduce viscosity, remove DNA, and remove insoluble material. This can be achieved most conveniently and effectively, while also removing some proteinaceous impurities, by addition of polyethyleneimine (Polymin P). To prevent RT from precipitating, the inert salt ionic strength of the suspension is first adjusted to from 0.025 M to 0.2 M, optimally to 0.15 M NaCl. To the suspension is added a volume of 5% (w/v) Polymin P to give a final concentration of 0.37% (w/v) to 0.54% (w/v), optimally 0.45% (w/v). After stirring for 15 minutes, the extract is freed of insoluble material by centrifugation.

To reduce the volume to a convenient level, the supernatant fluid containing dissolved enzyme and impurities is then brought to the minimum concentration of soluble inert salt, preferably, (NH$_4$)$_2$SO$_4$, necessary to maximally precipitate all of the active enzyme therefrom. It is preferred to add, to the aqueous solution of enzyme, crystalline (NH$_4$)$_2$SO$_4$ to about 35 to 50% saturation (45% optimally) by weight. This step, in addition to reducing the volume, effects the precipitation of enzyme and some proteinaceous impurities while leaving in solution a plurality of impurities. The precipitate containing the active enzyme is preferably removed from the medium by centrifugation and dissolved in an aqueous medium buffered to pH 7.5 and containing a suitable reducing agent, chelating agent, and nonionic detergent. The aqueous medium of this step preferably contains 10 to 50 mM, optimally 20 mM, Tris-HCl (pH 7.5), 1 mM dithiothreitol, 1 mM EDTA, 0.05-0.15 M NaCl, optimally 0.1 M, 5%–10% (v/v) glycerol, and nonionic detergent.

We have used ammonium sulfate to precipitate the enzyme because of its properties (high solubility in cold aqueous solutions, higher ionic strength than monovalent salts, etc.) which make it generally preferred. However those skilled in the art will recognize that other equivalent means may be found effective.

The solution containing dissolved enzyme is then clarified by centrifugation to remove any undissolved matter. RT is a hydrophobic protein that tends to bind to environmental surfaces during purification. In addition, during the practice of this invention subsequent to removal of nucleic acids, we have found that cloned M-MLV RT tends to form aggregates either through intramolecular binding of RT or through binding of RT to protein contaminants resulting in the precipitation of the enzyme in an enzymatically inactive form. As a result, it appears essential to provide the presence in the medium of a nonionic detergent. Any of a number of nonionic detergents can be used (Table 1). The concentration of the nonionic detergent in the medium should be below its critical micelle concentration, and nonionic detergents with high critical micelle concentrations, such as CHAPSO, CHAPS, or OG (Table 1), at a concentration of 0.01% to 0.1% (w/v), are preferred.

The solution should then be treated to remove excess precipitant salt (e.g., (NH$_4$)$_2$SO$_4$) and any dissolved low molecular weight (i.e., <100,000) cellular components dissolved therein. It is critically necessary that the precipitant be replaced with a suitable concentration of the inert salt since the active enzyme precipitates in the absence of a minimum concentration of salt.

The active enzyme precipitates during dialysis, so the reduction in salt concentration and removal of low molecular weight components operations are preferably effected by exclusion chromatography on a gel filtration column (e.g., Sephacryl S200, Bio-Gel P100) which has been previously equilibrated and eluted with an aqueous medium buffered to pH 7.5 (i.e., 20 mM Tris-HCl) containing reducing agent (i.e., 1 mM dithiothreitol), chelator (i.e., 1 mM EDTA), 0.05 to 0.15 M (optimally 0.1 M) monovalent salt (i.e., NaCl), 5% (v/v) glycerol, and optimally 0.01% w/v nonionic detergent.

The excluded salt concentration adjusted solution containing dissolved active enzyme is then preferably pumped directly to a chromatographic column comprising phosphocellulose (P-11) which adsorbs the active enzyme to the exclusion of certain nucleic acid and proteinaceous impurities. The column is previously equilibrated and after binding of the RT is washed with a suitable medium buffered to pH 7.5 (i.e., 20 mM Tris-HCl) and containing 1 mM dithiothreitol, 1 mM EDTA, 0.1 M NaCl, 5% (v/v) glycerol, and 0.01% (v/v) nonionic detergent.

A fraction containing the RT enzyme is eluted from the phosphocellulose with a linear salt gradient in medium buffered to pH 7.5 (i.e., 20 mM Tris-HCl) and containing 1 mM dithiothreitol, 1 mM EDTA, 5% (v/v) glycerol, 0.01% (w/v) nonionic detergent, and inert, soluble salt. The gradient runs from a low ionic strength of 0 to 0.15 M, optimally 0.1 M NaCl, to a high ionic strength of 0.4 to 0.8 M, preferably 0.5 M NaCl. The RT enzyme elutes as the major proteinaceous peak from the phosphocellulose column at 0.2 M to 0.3 M NaCl.

Phosphocellulose (P-11) by the manufacturer (Whatman) contains contaminants that inactivate M-MLV RT if the enzyme is adsorbed to unwashed phosphocellulose. In addition, the resin contains fines which must be removed to obtain workable column flow rates. It is necessary that the phosphocellulose be cycled through at least two and preferably three series of alkali-acid washes, and that it be defined extensively. The resin is suspended in 0.5 N NaOH at room temperature for 10 to 20 minutes. The alkali solution is removed by filtration and the resin is neutralized (to approximately pH 8) by extensive washing with deionized H$_2$O. The resin is then suspended in 0.5 N HCl at room temperature for 10 to 20 minutes. The acid solution is removed by filtration and the resin is neutralized (to approximately pH 4) by extensive washing with deionized H$_2$O. The process is repeated at least once and preferably two more times. The resin is then suspended in 1 to 2 M Tris-HCl (pH 7.5) at room temperature and if necessary is titrated with 0.4 N NaOH to pH 7.5. The Tris-HCl is removed by filtration and the resin is washed extensively with deionized H₂O. Resin is stored under chloroform at 4° C. The resin is defined extensively before use.

The monovalent salt concentration in the eluant fraction containing the RT from the phosphocellulose column is reduced to between 0.05 M and 0.15 M, optimally about 0.12 M, by the addition of an equal volume of an aqueous solution buffered to pH 7.5 (20 mM Tris-HCl) and containing 1 mM dithiothreitol, 1 mM EDTA, 5% (v/v) glycerol, and 0.01% (v/v) nonionic detergent.

The diluted eluant is further purified by contacting it with heparin-agarose or heparin-Sepharose in a chromatographic column whereby the active RT is preferentially adsorbed to the exclusion of practically all remaining proteinaceous impurities. The column is previously equilibrated with a suitable medium buffered to pH 7.5 (i.e., 20 mM Tris-HCl) and containing 1 mM dithiothreitol, 1 mM EDTA, 0.1 M NaCl, 5% (v/v) glycerol, and 0.01% (w/v) nonionic detergent. The column is washed extensively with a suitable medium buffered to pH 7.5 (i.e. 20 mM Tris-HCl) and containing 1 mM dithiothreitol, 1 mM EDTA, 5% (v/v) glycerol, 0.01% (v/v) nonionic detergent, and monovalent salt (i.e., NaCl) at a concentration of 0.2 M to 0.25 M NaCl. The duration and ionic strength of the wash are critical since the last traces of nuclease contamination are removed only with an extensive wash (10 to 25 column volumes, optimally 20 column volumes) with medium containing NaCl at a concentration within 0.01 M of the concentration required to begin RT elution from the heparin resin. The concentration at which RT begins to elute from heparin resin will be established empirically by means known to those skilled in the art; it depends upon the amount of heparin bound to the resin. For example, heparin agarose preparations containing 0.65 mg and 1 mg heparin bound per ml of resin were most effectively washed with medium containing NaCl at 0.2 M and 0.24 M, respectively.

A fraction containing the RT enzyme is eluted from the heparin resin with a linear salt gradient in medium buffered to pH 7.5 (preferably 20 mM Tris-HCl) and containing 1 mM dithiothreitol, 1 mM EDTA, 5% (v/v) glycerol, 0.01% (w/v) nonionic detergent, and an inert soluble salt. The gradient runs from a low ionic strength of 0.2 to 0.25 M to a high ionic strength of 0.5 to 1.5 M, optimally 1.0 M NaCl. The RT enzyme elutes as the only major proteinaceous peak from the heparin column at 0.2-0.25 M NaCl to 0.4 m NaCl.

The fraction from the heparin column containing the practically pure enzyme may be concentrated 2.5 to 3.5-fold and prepared for storage by dialysis against a medium buffered to from 7.5 to 8.0 (20 mM Tris-HCl) and containing reducing agent (1 mM dithiothreitol), chelator (0.1 mM EDTA), monovalent salt (0.1 M NaCl), nonionic detergent (0.01% (v/v) NP-40), and glycerol, 50% (v/v). The concentrated enzyme, buffered at pH 7.5 to 8.0 and in 45%-55% glycerol and 0.1 M NaCl, is stable for no less than 6 months at −20° C.

The enzyme purified by this method is capable of synthesizing a complementary DNA copy of a heteropolymeric single-stranded RNA or DNA template by successive addition of deoxyribonucleic acid moieties (dAMP, dCMP, dGMP, or TMP) complementary to the template and derived from dATP, dCTP, dGTP, or TTP to the 3′ terminal hydroxyl group of a ribo-or deoxyribopolymer primer annealed to the template. Cloned M-MLV RT purified by the method of invention also has ribonuclease H (RNase H) activity that specifically hydrolyzes the RNA of an RNA-DNA hybrid. This activity resides on the same polypeptide as the DNA polymerase activity. The enzyme is substantially free of contaminating ribonuclease and deoxyribonuclease activities. The denatured enzyme exhibits a single protein staining band after polyacrylamide gel electrophoresis with an apparent molecular weight of 80,000 (±5%) daltons.

It will be understood by those skilled in the art, having been exposed to the principles of the present invention as set forth hereinabove, that the concentration ranges for the various reagents utilized in the method of isolation of the enzyme include values which will result in the production of at least some enzyme, but that one may carry out the method operating somewhat outside those ranges with limited success with the costs attendant an inefficient operation. The appended claims, while setting forth the described ranges in the interests of adequatedly defining the invention, are intended to cover values which differ only insignificantly therefrom but which result in production of at least some enzyme.

METHODS AND EXAMPLES

The following methods and examples are set forth to further disclose techniques relating to the practice of the presently preferred embodiments of the invention, and to provide illustrations of the invention. They are not to be construed as limiting the scope of the invention in any manner, beyond that scope determined by the appended claims. Various modifications in the described practice of the invention, but within its spirit and scope, will occur to those of skill in the arts to which it pertains.

(a) Materials and General Methods

Enzymes were from Bethesda Research Laboratories. Poly and oligonucleotides were from P-L Biochemicals. Goat antiserum prepared against Rauscher MLV RT was furnished by Dr. D. Grandgenett. Goat antiserum against PolIK was furnished by Dr. N. Grindley. IgG from serum was prepared by chromatography on DEAE-cellulose followed by (NH₄)₂SO₄ precipitation and dialysis against 0.1 M Tris HCl(pH8.0).

Bacterial strains used included E. coli HB101, LE392, and K802(Maniatis, et al.; Molecular Cloning. A Laboratory Handbook, Cold Spring Harbor Laboratory, Cold Spring Harbor, NY, 1982), and 2077. The latter is a lon⁻ strain derived from BNN96, which is a derivative of SG1041 and contains the lon-100 allele (Young, R.A. and Davis, R.W.; Efficient isolation of genes by using antibody probes. Proc. Natl. Acad. Sci. USA 80 (1980) 1194–1198). E. coli strains K802 (Maniatis, et al., 1982) and 2077 (Kotewicz, M. L., D'Alessio, J. M., Driftmier, K. M., Blodgett, K. P., and Gerard, G. F. (1985). Cloning and over expression of Moloney murine leukemia virus reverse transcriptase in Escherichia coli. Gene 35, 249–258.) carrying a λ lysogen (λ cIindlts857 S7; Hendrix, R. W., Roberts, J. W., Stahl, F. W., Weisberg, R. A. (1983). Lambda II. Cold Spring Harbor Laboratory, Cold Spring Harbor, N.Y.) were used to construct and maintain pRT210-derived plasmids. lon− derivatives of K802(λ) carrying a pRT300 or pRT600 series plasmid were constructed utilizing a lon gene inactivated by insertion of the transposon mini-TN5 near the 5′ end of the gene. Phage P1 vir was grown on E. coli SG20322 and used to transduce K802(λ) containing a pRT300 or pRT600 series plasmid to tetracycline resistance. The lon− genotype of each construct was verified by the overproduction of capsular polysaccharides which results in mucoidy.

Bacteria were grown in TYN medium containing 1.0% tryptone, 0.5% yeast extract and 0.5% NaCl, plus 50 μg ampicillin/ml. Plasmid pGW8 was kindly supplied by Dr. G. Wilson. A recombinant clone (390) of phage λ Charon 21A and circular M-MLV proviral DNA joined at the unique HindIII site of each was supplied by Dr. S. Tronick (Tronick, S. R., Robbins, K. C., Canaani, E., Devare, S.G., Andersen, P. R. and Aaronson, S. A.; Molecular cloning of Moloney murine sarcoma virus; arrangement of virus-related sequences within the normal mouse genome. Proc. Natl. Acad. Sci. USA 76 (1979) 6314–6318.)

[$^{35}$S]Methionine labeling of cells was performed in M56 minimal medium (Gottesman, M. E. and Yarmolinsky, M. B.; Integration-negative mutants of bacteriophage lambda. J. Mol. Biol. 31 (1968) 487-495.) supplemented with 0.2% glucose and 0.2 mM mixture of essential amino acids minus methionine. Cells at an $A_{595}$ of 0.4 were labeled with 20μ Ci [$^{35}$S]methionine (400 Ci/mmol; Amersham) per ml of culture.

Plasmid DNA was prepared from bacteria by the method of Birnboim and Doly (Birnboim, H. C. and Doly, J.; A rapid alkaline extraction procedure for screening recombinant plasmid DNA. Nucl. Acids Res. 7 (1979) 1513–1523.). In some cases DNA was further purified by banding in CsCl-EtBr gradients (Maniatis et al., 1982). Nucleotide sequencing was performed by published methods (Maxam, A. M. and Gilbert, W.; Sequencing end-labeled DNA with base-specific chemical cleavages. Methods Enzymol 65 (1980) 499–560.) (Messing, J.; New M13 vectors for cloning. Methods Enzymol. 101C (1983) 20–89.). Electrophoresis of proteins was performed on 6 to 15% linear gradient polyacrylamide gels or 7% gels by the procedure of Laemmli (Laemmli, U. K.; Cleavage of structural proteins during the assembly of the head of the bacteriophage T4. Nature 227 (1970) 680–685.). Unlabeled proteins were stained with Coomassie Blue (Grandgenett, D. P. et al., (1973). A single subunit from avian myeloblastosis virus with both RNA-directed DNA polymerase and ribonuclease H activity. Proc. Natl. Acad. Sci. USA 70, 230–234.) and [$^{35}$S]methionine-labeled proteins were detected by fluorography (Laskey, R. A.; the use of intensifying screens or organic scintillators for visualizing radioactive molecules resolved by gel electrophoresis. Methods Enzymol 65 (1980) 363–371.). To quantitate radio-labeled protein bands, exposed film was used as a template to excise regions of interest from gels. Gel pieces were extracted in organic scintillation fluid containing 3% Protosol (NEN) at 37° C. for 18 hours and counted. To quantitate stained protein bands, gels were scanned with an LKB Laser Densitometer equipped with a Hewlett Packard Integrator. Protein concentrations were determined by the method of Bradford (Bradford, M. M. (1976). A rapid and sensitive method for the quantitation of microgram quantities of protein utilizing the principle of protein-dye binding. Anal. Biochem. 72, 248–254.) with bovine serum albumin as standard.

The procedures for the isolation of plasmid DNA, cleavage with restriction enzymes, isolation of DNA fragments, digestion with Bal-31 nuclease, filling in DNA recessed 3' ends with PolIK, ligation with T4 DNA ligase, and transformation and growth of E. coli were standard procedure as previously described (Kotewicz, et al., 1985.). Plasmid pRT103 was constructed from pRT210 as described previously (Kotewicz, et al., 1985.).

(b) Preparation of Cell Extracts

Unlabeled cells were first lysed at 4° C. under conditions such that cellular DNA was removed by sedimentation at low speed (Godson, G. N. and Sinsheimer, R. L.; Lysis of Escherichia coli with neutral detergent. Biochim. Biophys. Acta 149 (1967) 476–488.). This was followed by two more extraction steps at 4° C. using different extraction buffers. Step 1: washed cells suspended in 80 μl of 25% sucrose and 10 mM Tris-HCl (pH8.0) per ml of starting culture were lysed by addition of 20 μl of a 1:1 mixture of 0.85 mg/ml lysozyme in 0.25 M Tris-HCl (pH 8.0) and 8 mM EDTA (pH 8.0) followed by 100 μl of 1% (v/v) Triton X-100, 20 mM $MgSO_4$, and 2 mM Tris HCl (pH 8.0); the suspension was centrifuged at 10000 x g for 5 min, and the supernatant was saved (soluble fraction). Step 2: the pellet was extracted with 200 μl of 2% (v/v) NP-40, 0.1% (w/v) Na deoxycholate, 20 mM Tris HCl (pH 8.0), 2 mM DTT and 1 mM EDTA and centrifuged; the supernatant was designated the high-detergent fraction. Step 3: the remaining pellet was extracted with 200 μl of 1% (w/v) SDS, 1% (v/v) Triton X-100, 0.5% (w/v) Na deoxycholate, 0.01 M $NaPO_4$ (pH 7.4), 0.1 M NaCl, and 0.001 M PMSF and centrifuged. The supernatant was saved (residual fraction).

[$^{35}$S]Methionine-labeled cells were disrupted at 4° C. with lysozyme and extracted with the SDS-containing buffer described above.

(c) Immunoprecitation of Labeled Proteins

M-MLV RT-related proteins were immunoprecipitated from E. coli extracts by the staphylococcal protein-A-antibody adsorbent method of Kessler (Kessler, S. W.; Rapid isolation of antigens from cells with Staphylococcal protein A-antibody adsorbent; parameters of the interaction of antibody-antigen complexes with protein A. J. Immunol. 114 (1975) 1617–1624.). Goat antiserum to MLV RT was preadsorbed with the 100000 x g supernatant from an extract of plasmid-free E. coli strain 2077 grown at 30° C.

(d) Enzyme Assays

RT activity in crude extracts was assayed utilizing poly(2'-0-methylcytidylate).oligodeoxyguanylate [$(Cm)_n \cdot (dG)_{12-18}$] (Collaborative Research), a template-primer specific for RT and not copied by the DNA polymerases in E. coli (Gerard, G. F., et al., (1974) Poly (2'-0-methylcytidylate).oligodeoxyguanylate as template for the RNA directed DNA polymerase in RNA tumor virus particles and a specific probe for the RNA directed enzyme in transformed murine cells. Biochem. 13, 1632–1641.; Kotewicz, et al., 1985). Two μl aliquots from extracts were incubated in 50 μl reaction mixtures for 10 min at 37 C. Reaction mixtures contained 20 μM Tris-HCl (pH 8.0), 1 mM dithiothreitol (DTT), 100 mM KCl, 2 mM $MnCl_2$, 50 μM [$^3$H]dGTP (150 cpm/pmole), 50 μM $(Cm)_n$, and 20 μM $(dG)_{12-18}$. Acid insoluble product was determined on Whatman GF/C glass fiber filters.

To establish specific activities of purified RT preparations, activity was assayed with $(A)_n \cdot (dT)_{12-18}$ (Houts, G. E., et al. (1979). Reverse transcriptase from avian myeloblastosis virus. J. Virol. 29, 517–522.). One unit is defined as the amount of enzyme that incorporates one nmole of TMP into acid insoluble product in 10 min at 37° C. Reaction mixtures (50 μl) contained 50 mM Tris-HCl (pH 8.3), 6 mM MgCl$_2$, 40 mM KCl, 500 μM [$^3$H]TTP (30 cpm/pmole), 1 mM DTT, 100 μg/ml bovine serum albumin, 100 μM (A)$_n$ and 100 μM (dT)$_{12-18}$.

RT RNase H activity was assayed with [$^3$H](A)$_n$·(dT)$_n$ (Gerard, G. F. and Grandgenett, D. P. (1975). Purification and characterization of the DNA polymerase and RNase H activities in Moloney murine sarcoma-leukemia virus. J. Virol. 15, 785–797.). E. coli DNA polymerase I activity in extracts was assayed using (dA)$_n$·(dT)$_{12-18}$ as a primer template (Tamblyn, T. M. and Wells, R. D.; Comparative ability of RNA and DNA to prime DNA synthesis in vitro; role of sequence, sugar, and structure of template-primer. Biochemistry 14 (1975) 1412–1425.).

EXAMPLE 1: Construction of Expression Vector Plasmid pKD1 (see also FIG. 1)

First, plasmid pGW8 was derived from pBR322 and phage λ in two steps. The BamH I - EcoR I restriction fragment of λ containing the phage immunity region and major promoters (Hendrix, et al., 1983) was ligated into the BamH I - EcoR I large fragment of pBR322. Genes cI, cro and cII, as well as the rightward promoter, p$_R$ were removed by Bgl II digestion to create pGW8. This plasmid and its derivatives are maintained at 30° C. in bacterial strains that carry a ts mutant cI gene supplied by a resident λ lysogen (λ cI indl ts857 S7; Hendrix, R. Q., Roberts, J. W., Stahl, F. W. and Weisberg, R. A.; Lambda II. Cold Spring Harbor Laboratory, Cold Spring Harbor, NY, 1983.) to maintain plasmid stability and to modulate transcription from the p$_L$ promoter (Bernard, H.U. and Helsinki D. R.; Use of the λ phage promoter p$_L$ to promote gene expression in hybrid plasmid cloning vehicles. Methods Enzymol. 68 (1979) 482–492.; Remaut, E., et al., Plasmid vectors for high-efficiency expression controlled by the p$_L$ promoter of coliphage lambda. Gene 15 (1981) 81–93.)

The Nde I site in the pBR322 region of pGW8 was deleted by digestion with Nde I and Sal I transforming E. coli K802 λ with linear DNA. A transformant, pKDO, was identified which by restriction enzyme analysis was found to be missing approx. 200 bp from the junction of the Nde I and Sal I sites.

Finally, an RBS fragment derived from the λ cII gene (Sau 3A to Hae III fragment of λ, map position 38475 to 38150) which contained a Nde I site was then inserted into pKDO between the unique Hpa I and BamH I sites, bringing p$_L$, the RBS, and a unique Nde I site into the desired arrangement. E. coli K802 λ transformants were screened for plasmids containing an Nde I site. One plasmid, pKD1, was identified by nucleotide sequencing (Maxam and Gilbert, 1980) and had been correctly joined at the Hpa I and Hae III blunt ends. Maps of λ are oriented opposite to the conventional λ map.

EXAMPLE 2: Construction of Gene Source Plasmid pRT1

Figure 3:
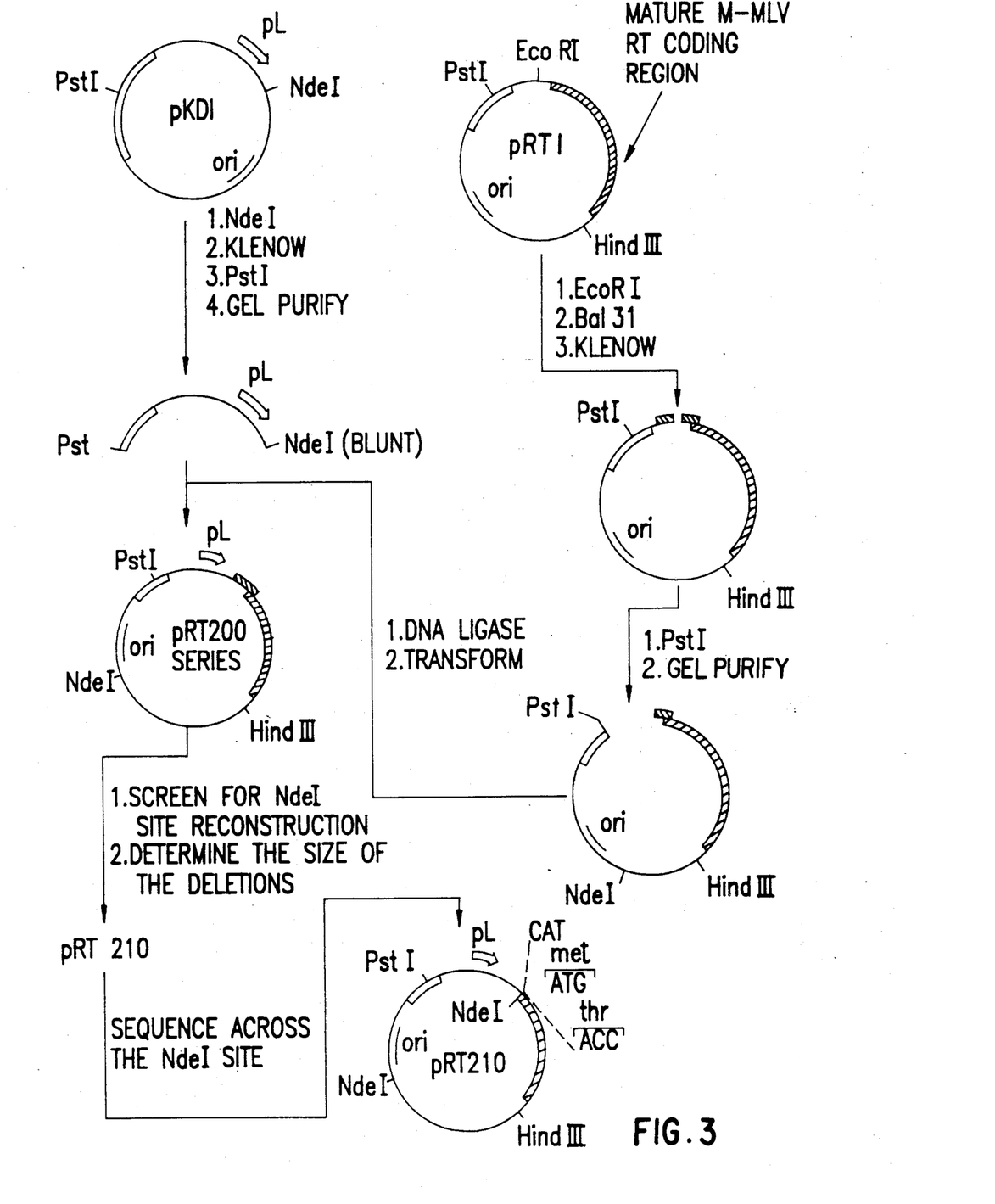
FIG. 3 is a schematic illustration showing the preparation of a preferred preliminary vector, pRT210.

DNA from Charon 21A, containing the M-MLV proviral DNA inserted at its unique Hind III site, was cut with Sst I at position 2558 of the M-MLV sequence (Shinnick, T. M., et al.; Nucleotide sequence of Moloney murine leukemia virus. Nature 293 (1981) 543–548.), the 3' extension was blunted with T4 polymerase (Challberg, M. D. and Englund, P. T.; Specific labeling of 3' termini with T4 DNA polymerase. Methods Enzymol 65 (1980) 39–43.) and the DNA was cleaved with Hind III at position 4894 (Shinnick, et al., 1981). This liberated a 2336-bp fragment which contained the entire coding region of the mature RT (positions 2598-4610 of the M-MLV genome; FIG. 2B). The 2336-bp fragment was cloned into pBR322 between its EcoR I and Hind III sites by cutting pBR322 DNA with EcoR I, repairing with PolIK, cutting with Hind III, and ligating with an excess of the M-MLV 2336-bp fragment. The resulting plasmid (pRT1) contained a reconstructed EcoR I site allowing convenient access to the 5' region of the cloned DNA (FIG. 3).

EXAMPLE 3: Construction of Preliminary Vector Plasmid pRT210 from pKD1 and pRT1 (see also FIG. 3)

pRT1 was cleaved with EcoR I and digested with BAL 31 nuclease, repaired with PolIK, and cleaved with Pst I. The larger fragments (approx. 5.9 kb) were agarose-gel-purified. pKD1 was cleaved with Nde I, repaired with PolIK, and cleaved with Pst I. The 1.7-kb fragment containing p$_L$ was purified by agarose gel electrophoresis, and was ligated with the approx. 5.9-kb BAL-treated fragments. 13 Ap$^R$ clones containing a reconstructed Nde I site were analyzed to determine the extent of the deletions at the 5' end of the M-MLV DNA. One plasmid was identified (pRT210) which contained the correct size deletion (Nde I site reconstruction at position 2596 of the M-MLV sequence; FIG. 2B). The DNA sequence at the Nde I site reconstruction was confirmed by DNA sequence analysis.

In pRT210, an ATG initiation codon is adjacent to the ACC triplet at the beginning of the gene. The 284-bp sequence in pRT210 between the 3' end of the DNA sequence coding for mature M-MLV RT and the Hind III site contains no in-frame translation termination codons (Shinnick, et al., 1981).

EXAMPLE 4: Construction of Terminator Source Plasmid pBRT

Plasmid pBRT (FIG. 4) was constructed from plasmids pBR322 (Maniatis, et al., 1982) and pUC9 (Vieira, J. and Messing, J. (1982). The pUC plasmids, an M13 mp7-derived system for insertion mutagenesis and sequencing with synthetic universal primers. Gene 19, 259–268.) in two steps. First, a universal terminator fragment (P-L Biochemicals) was inserted into Sma I site of the multiple cloning region of pUC9 (Lathe, R. et al. (1984). Linker tailing: unphosphorylated linker oligonucleotides for joining DNA termini. DNA 3, 173–182.). A Sal I - Sca I fragment from the resulting terminator-containing plasmid was then ligated with the Sal I - Sca I fragment of pBR322 that contained the origin region. The resulting plasmid, pBRT, was propagated in E. coli HB101 (Maniatis, et al., 1982).

EXAMPLE 5: Construction of pRT300 and pRT600 Series Plasmids (see also FIG. 4)

pRT210 (Example 3) was cleaved with Hind III, digested with Bal-31 nuclease for 3 or 6 min (generating the pRT300 and pRT600 series, respectively), repaired with PolIK, and cleaved with Pst I. The ~2.7 Kb fragments were agarose gel purified. pBRT (Example 4) was cleaved with EcoR I, repaired with PolIK, and cleaved with Pst I. The Pst I - EcoR I fragment, which contained a unique Sal I site and a universal terminator sequence just inside the EcoR I site, was purified by agarose gel electrophoresis.

The pBRT fragment was ligated separately with the ~2.7 kb fragments generated from pRT210. E. coli K802(λ)-transformed, ampicillin-resistant recombinant clones were screened for the size of the BAL 31 nuclease deletion by cleaving with Sal I, repairing recessed 3' ends with PolIK and dGTP, dCTP, dTTP, and [α-$^{32}$P]dATP, cleaving inside the RT gene with an appropriate restriction enzyme, and either sizing by polyacrylamide gel electrophoresis or sequencing the appropriate labeled DNA fragment. Digestion with Bal-31 nuclease for 3 and 6 minutes produced average deletions in the M-MLV DNA of approximately 200 and 400 base pairs, respectively.

EXAMPLE 6: Use of the pRT300 and pRT600 Series Plasmids in the Production of RT Enzymes A. Growth and Induction of E. coli Carrying pRT210 and its Derivatives.

Unlabeled K802(λ) cells carrying pRT210 derivatives in 10 ml of 2X TYN+ampicillin medium (Kotewicz et al., 1985) were grown to an $A_{595}$ of 0.4 at 30° C. They were transferred to a shaking water bath and incubated at 42° C. for 15 minutes to inactivate λ cI repressor (Hendrix et al., 1983) and then 36° C. for 75 minutes, and were harvested by centrifugation. 2077(λ) cells were grown at 36° C. for only 45 minutes subsequent to a 15 minute induction.

Cells to be labeled with [$^{35}$S]methionine were first grown in a 10 ml culture in 2X TYN+ampicillin medium to an $A_{595}$ of 0.25 at 30 C. After harvesting in one ml aliquots by centrifugation, each cell pellet was resuspended in one ml of M56 minimal medium (Gottesman and Yarmolinsky, 1968) supplemented with 0.2% glucose, 0.2 mM amino acids minus methionine, and 50 μg/ml ampicillin. After incubating in a shaking water bath at 30° C. for 1 hour and at 42° C. for 15 min, 100 to 200 μCi of [$^{35}$S]methionine (400 Ci/mmole; Amersham) were added, and cells were placed at 36° C. After 2 minutes, a 250 μl aliquot was removed and immediately frozen, and 80 μl of 5 mM methionine (1000-fold excess) was added to the remaining 750 μl. Incubation was continued at 36° C. and 250 μl aliquots were removed and frozen at various times. Aliquots were thawed and cells pelleted just before extraction.

B. Purification of RT from K802(λ) Cells Carrying pRT210-Derived Plasmids.

Cells were grown to an $A_{595}$ of 0.8 at 32° C., induced at 42° C. for 45 minutes, and then grown at 37° C. for three hours before harvesting. RT was extracted from 10 g of cells suspended in 100 ml of 20 mM Tris-HCl (pH 7.5), 1 mM EDTA, 25 mM NaCl, 0.1 mM phenylemethylsulfonyl fluoride, and 1 mM DTT by addition of a ml of 13 mg/ml lysozyme and 1 ml of 10% sodium deoxycholate, followed by homogenization with a Turrax homogenizer. After centrifugation at 10,000 X g for 30 minutes, nucleic acids were removed from the supernatant by precipitation with 2.5 ml of 10% Polymin P (Jendrisak and Burgess, 1975). RT was then precipitated by addition of solid $(NH_4)_2SO_4$ to 40% saturation. The pellet was dissolved in 5 ml of 20 mM Tris-HCl (pH 7.5), 1 mM EDTA, 100 mM NaCl, 1% NP-40, 0.1% sodium deoxycholate, and 20% ethylene glycol and the extract desalted on a 90 ml BioGel P6-D column run in buffer A (20 mM Tris-HCl, pH 7.5, 1 mM DTT, 1 mM EDTA, 0.01% NP-40, and 5% glycerol) plus 0.1 M NaCl. The sample was loaded on a 5 ml column of phosphocellulose equilibrated in buffer A+0.1 NaCl; the column was washed with the same buffer and eluted with a 20 ml linear gradient of 0.1 M to 0.4 M NaCl in buffer A. The RT peak was pooled, diluted with an equal volume of buffer A, and loaded on a Mono-S HR 5/5 column (Pharmarcia) equilibrated in buffer A. RT was eluted with a 20 ml concave gradient of 0.1 M to 0.3 M NaCl in buffer A. 20-30% of the RT units in the homogenate were recovered.

EXAMPLE 7: Studies of the RT Enzymes Produced by the pRT300 and pRT600 Plasmids

Crude extracts were prepared from induced K802(λ) cells carrying the pRT300 and pRT600 plasmids and the extracts were assayed for RT activity. Table 1 shows that RT levels in cells fell into two relatively narrow ranges: low (1,214–1,748 cpm incorporated/2 μl) and high (7,335–8,857 cpm incorporated/2 μl). With the exception of pRT308, only plasmids with the terminator within 10 to 20 nucleotides of the 3' terminus produced RT activity in the high range.

There are at least three parameters that could vary with the cloned RT carboxy terminus location and as a consequence influence the RT activity levels observed in E. coli. These are the solubility, intrinsic enzyme specific activity, and stability or resistance to proteolytic breakdown of cloned RT.

The solubility of RT expressed from each of the plasmids listed in Table 1 in E. coli K802(λ) was established. Solubility of RT in E. coli K802(λ) was independent of carboxy-terminal structure; enzyme expressed from each plasmid in Table 1 was greater than 90% soluble in neutral detergent.

In order to examine the correlation between enzyme specific activity and RT structure, enzyme was purified from E. coli K802(λ) cells bearing plasmid pRT601, pRT305, or pRT603 (Table 1). Purification was by phosphocellulose chromatography and Mono-S FPLC. Enzyme unit concentrations and protein concentrations were determined, and purity was assessed by SDS polyacrylamide gel electrophoresis. RT molecular weights ($M_r$) deduced from the DNA sequences of pRT601, pRT305 and pRT603 are 78,000, 82,000 and 70,000, respectively. The pRT601 and pRT305 preparations contained major protein bands of 79,000 and 82,000, respectively, and after taking into consideration the percentage of total protein present in these bands, the enzyme specific activities were calculated to be 430,000 and 450,000 units/mg, respectively.

The largest and major proteins found in the pRT603 RT preparation had $M_r$=62,000 and 57,000. The simplest assumption is that these are proteolytic breakdown products of an $M_r$=70,000 enzyme, and are the enzymatically active RT species in the preparation. Enzymatically active forms of murine RT of this size have frequently been obtained in preparations of enzyme purified from virus (Gerard and Grandgenett, 1975; Moelling, K. (1976). Further characterization of the Friend murine leukemia virus transcriptase - RNase H Complex. J. Virol. 18, 418–425). The specific activity of the pRT603 RT was 230,000 units/mg, similar to the other two enzymes. M-MLV RT with an $M_r$=80,000 purified from virus has a specific activity of 240,000 units/mg. Because purified, cloned RTs with a spectrum of carboxy termini have specific activities within a factor of 2 of purified viral RT, differences in specific activities cannot explain the correlation observed in Table 1 between RT carboxy terminus location and RT activity levels in E. coli.

Figure 5A:
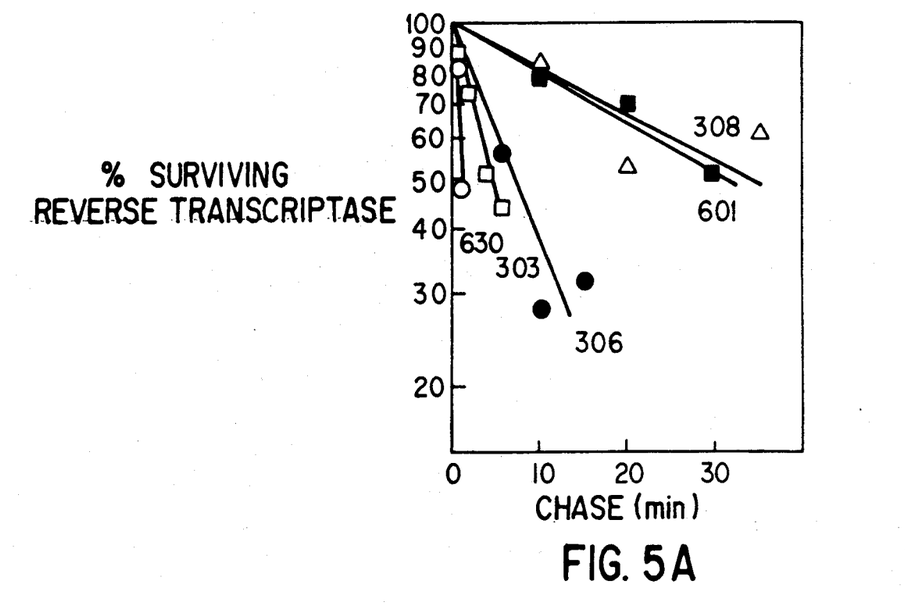
FIG. 5 is a set of graphs showing the results of pulse-chase experiments to determine the half-lives of the RT enzymes produced in *E. coli* K802(λ) carrying the preferred pRT300 and pRT600 vectors.
Figure 5B:
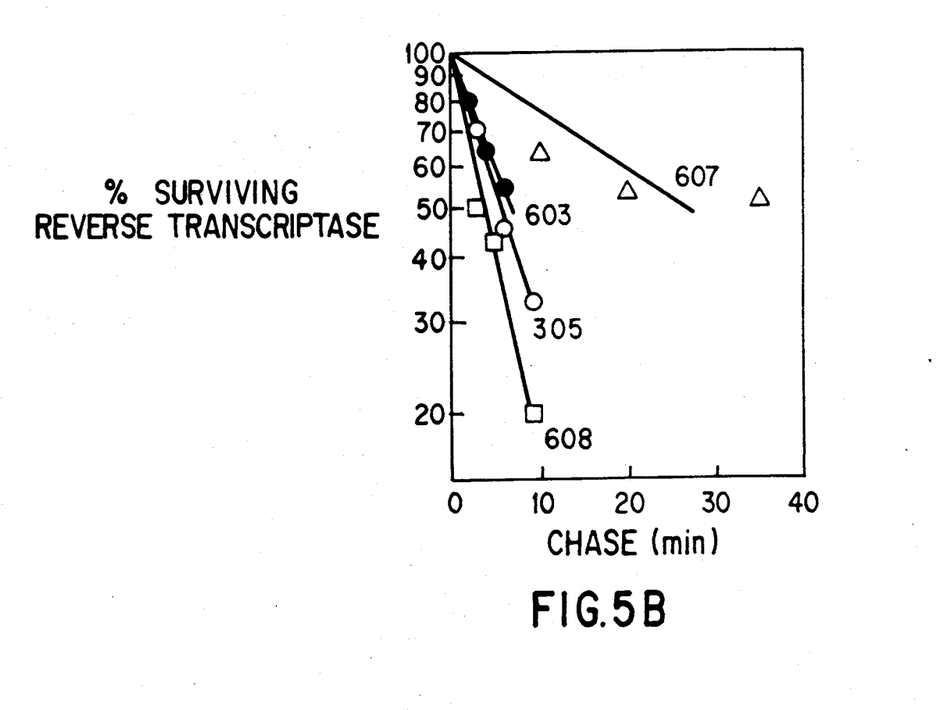

The half lives of RTs synthesized in E. coli were established to ascertain if there was any relationship between RT carboxy-terminal structure and stability in E. coli. E. coli K802($\lambda$) carrying one of the pRT300 or pRT600 plasmids was induced, labeled for 2 minutes with [$^{35}$S]methionine, chased with an excess of cold methionine, and sampled at various times during the chase. Labeled proteins immunoprecipitated from cell extracts with anti-RT serum were run on SDS polyacrylamide gels. RT bands in the 70K to 80K Mr range that diminished at different rates during the chase were seen in the immunoprecipitates from cells carrying the pRT300 and pRT600 plasmids. Intact RT bands excised from gels were counted and the percent of RT that survived during the chase was plotted versus the chase duration (FIG. 5A and B). The half lives of RT expressed from the pRT300 and 600 series plasmids were established from these plots and are listed in Table II. There was a good correlation between the half life of RT and the level of RT enzyme activity in cells. Plasmids producing low levels of RT activity coded for RTs with half lives in the 2 to 7 minute range. High levels of RT activity were produced by enzymes with half lives of 26 to 35 minutes.

Figure 5C:
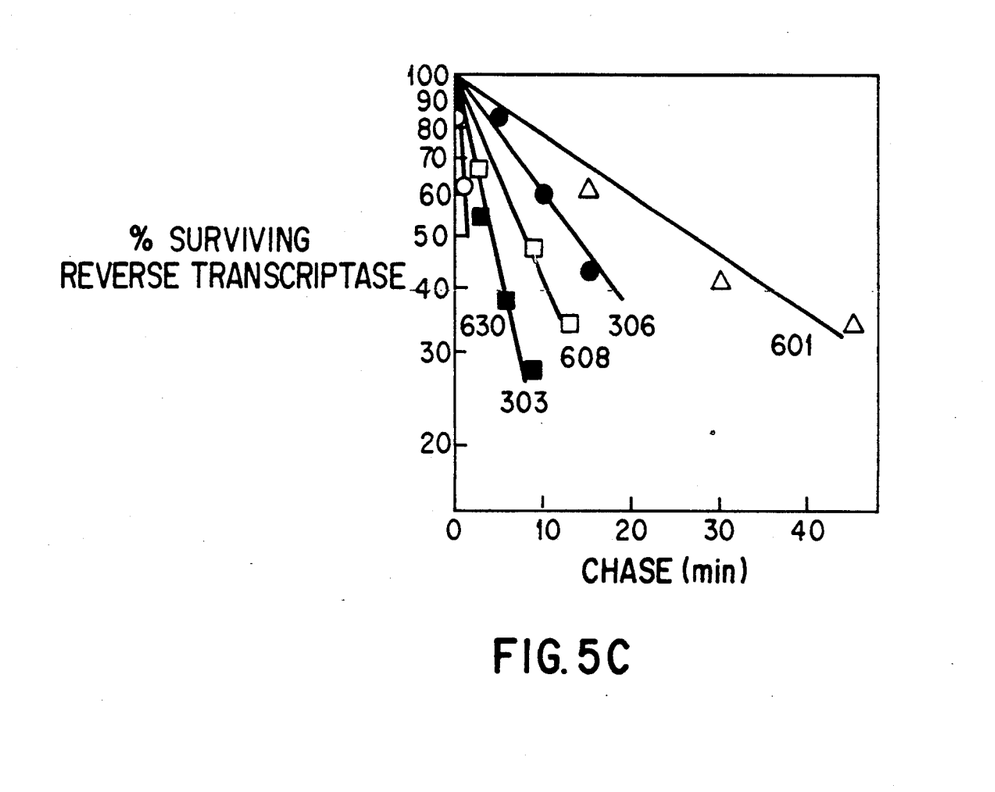

Protease La, the gene product of the lon locus in E. coli, catalyzes an initial ATP-dependent, rate-limiting step in the degradation of abnormal proteins (Chung, C. H. and Goldberg, A.L. (1981). The product of the lon (cap R) gene in Escherichia coli is the ATP-dependent protease, protease La. Proc. Natl. Acad. Sci. U.S.A. 78, 4931-4935). We compared the stabilities of RT coded by pRT630, 608, 601, 306, and 303 in E. coli K802($\lambda$) lon− cells (FIG. 5C). The half lives of RT coded by pRT630, 601, and 303 were unchanged in lon− cells, but RT coded by either pRT608 or pRT306 was twice as stable in lon− as in lon+ E. coli (Table II). These results may mean that in general protease La does not play a major role in the degradation of cloned RT in E. coli K802($\lambda$), and that the decreased stability of RT coded by pRT608 and 306 in lon+ versus lon− cells might be explained by the presence of a protease La site near the carboxy end of each of these RTs. Recent model substrate studies with oligopeptides indicate one characteristic of a potential protease La cleavage site is the presence of a phenylalanine with an acidic residue located several amino acids to its amino side (Waxman, L. and Goldberg, A.L. (1985). Protease La, the lon gene product, cleaves specific fluorogenic peptides in an ATP-dependent reaction. J. Biol. Chem. 260, 12022-12028). One structural feature shared by RT coded by pRT608 and 306, the RTs stabilized in lon− cells, but missing in the carboxy ends of RT from pRT630, 601, and 303, is the presence of a phenylalanine and an aspartic acid located 5 residues to the amino side of the phenylalanine. These structural arrangements of aspartic acid and phenylalanine were created fortuitously during plasmid construction by the introduction of a universal terminator sequence at random points near the carboxy end of the RT gene. Cleavage at a carboxy-terminal site by itself probably would not destabilize RT, but the carboxy-terminal site might provide a readily accessible binding site for protease La from which it could more rapidly find RT inactivating cleavage sites by moving along the polypeptide chain (Goldberg, A.L. and Waxman, L. (1985). The role of ATP hydrolysis in the breakdown of proteins and peptides by protease La from Escherichia coli. J. Biol. Chem. 260, 12029-12034).

Figure 6A:
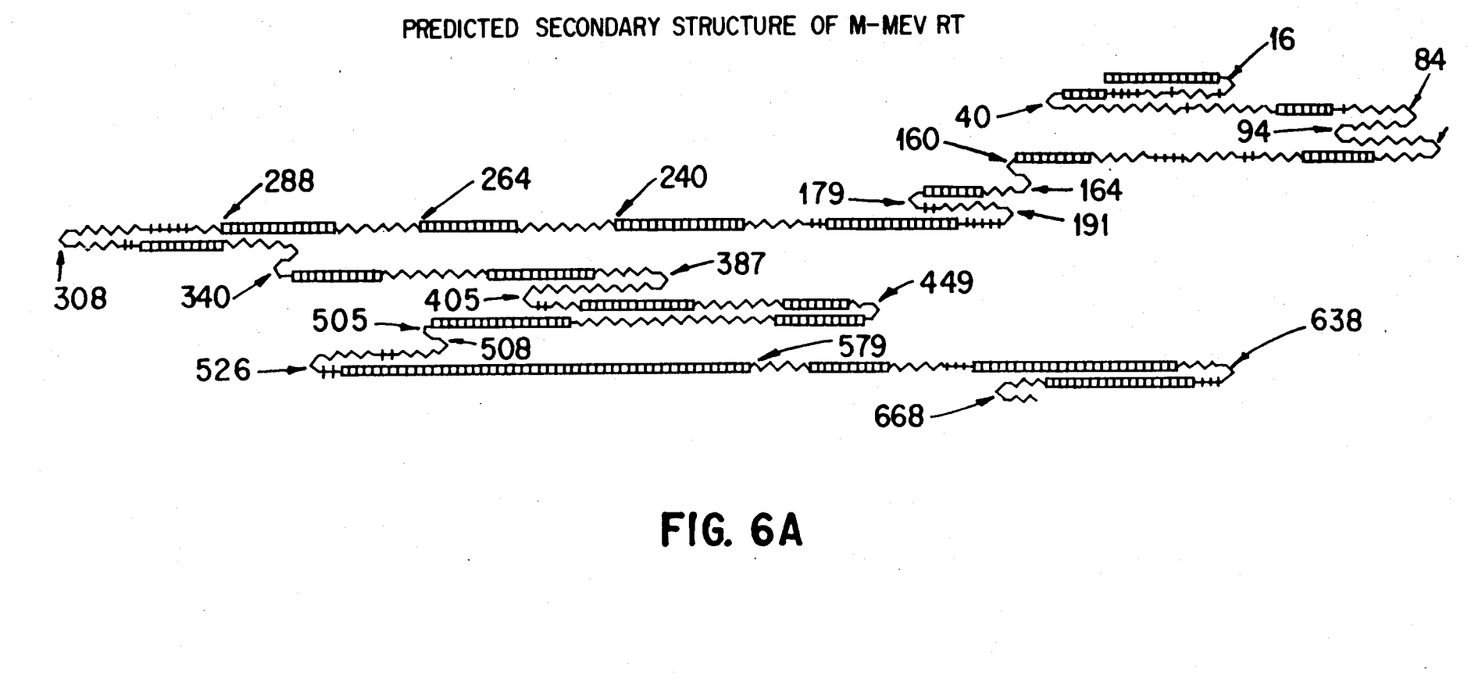
FIG. 6 is a set of diagrams showing predictions of the secondary structures of (A) viral M-MLV RT and (B) the carboxy ends of the RT proteins coded by the preferred RT vectors, as compared to their activities and half lives.
Figure 6B:
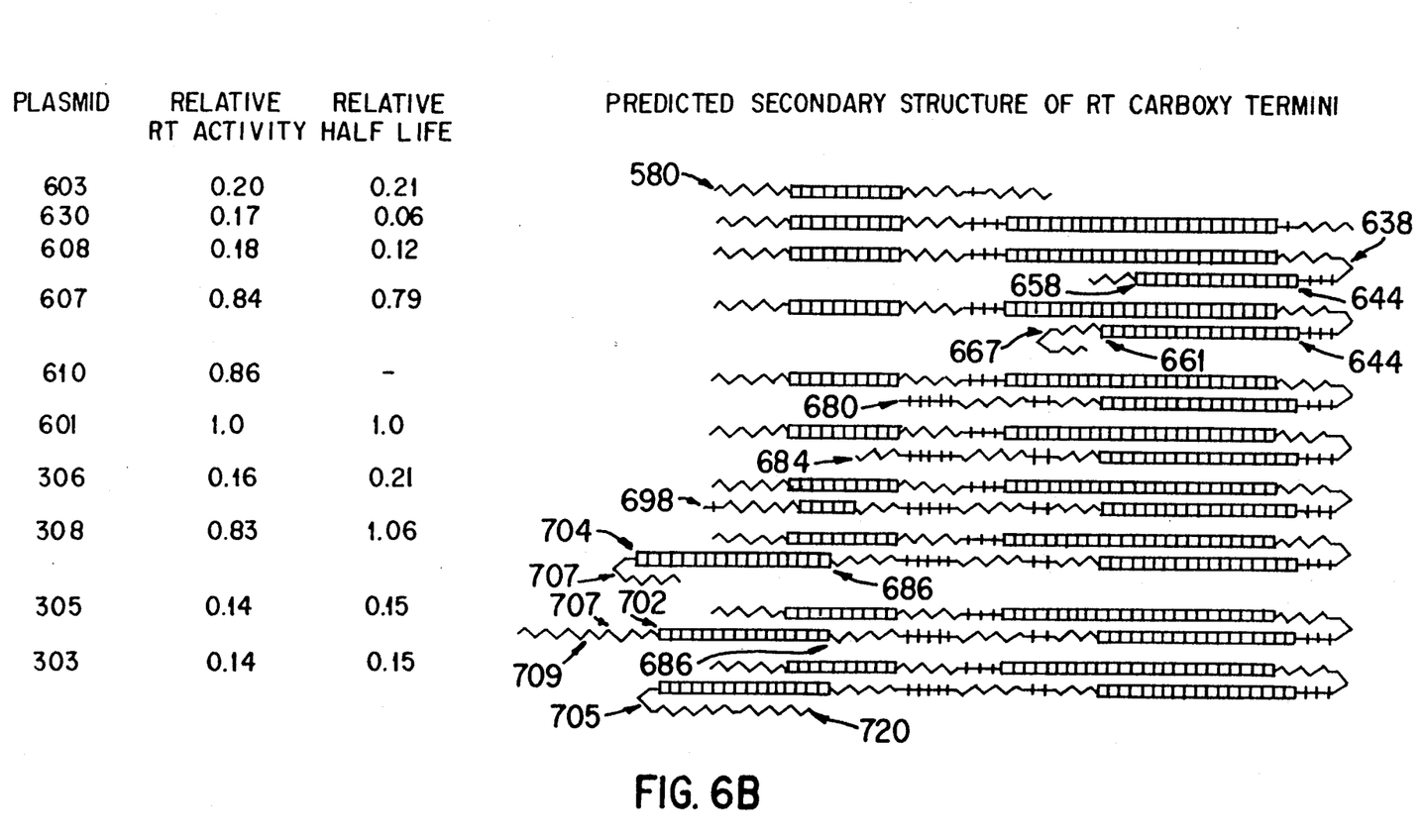

To gain insight into the relationship between stability and carboxy-terminus structure, the computerized method of Garnier et al. (1978) was used to predict the secondary structure of the carboxy termini of cloned RTs. This method assigns amino acids one of four conformational states: $\alpha$-helix, $\beta$-pleated sheet, $\beta$-turn, or random coil. The method predicts that M-MLV RT has a high proportion of ordered structure: 44% $\alpha$-helix and 37% $\beta$-pleated sheet (FIG. 6A). The predicted secondary structures of RT carboxy termini coded by the pRT300 and pRT600 plasmids are shown in FIG. 6B. Close examination of the secondary structures of the RTs found at stability transition points, i.e. pRT603 to 607 (6.5-fold stability increase), pRT601 to 306 (4.7-fold decrease), pRT306 to 308 (5-fold increase), and pRT308 to 305 (7-fold decrease) reveals that the one structural feature common to the more stable RTs but missing in the less stable enzymes in each transition pair is the presence of an $\alpha$-helix containing 18 amino acids adjacent to the carboxy terminus. For example, the primary amino acid sequence of RT from pRT305 is identical to that of RT coded by pRT308, with the exception that the triplet Try-Trp-Val has been introduced between amino acid 706 and 707. Introduction of these 3 hydrophobic amino acids reduced the length of the predicted carboxy terminal -helix by 2 amino acids and the stability of RT by a factor of 7. Other less stable RTs, such as pRT603, 630, and 303 have -helices adjacent to the carboxy terminus shorter or longer than 18 amino acids (FIG. 6B).

EXAMPLE 8: The Large-Scale Preparation of Cloned M-MLV Reverse Transcriptase

E. coli strain N4830 (derived by lysogenizing E. coli strain SA1615 with lambda xisl; see Gottesman, et al., 1980) is used as the preferred host. A deposit of a culture of cell line E. coli N4830 bearing the disclosed plasmid, pRT601 of this invention, has been made in the American Type Culture Collection in Rockville, Md., and assigned Accession No. 67007.

This cell line produces commercially useful quantities of active reverse transcriptase enzyme. Fifty $\mu$l of a seed culture of 4380 (pRT601) cells (approximately $10^{10}$ cells) in inoculated into 100 ml of medium (20 g/l tryptone, 10 g/l yeast extract, 10 g/l NaCl, and 50 $\mu$g/ml ampicillin) incubated with shaking at 30° C. for 6 hr. Ten ml of the culture is inoculated into 15 liter of medium in a 20 liter Chemap fermentor. Cells are grown at 30° C. for 16 hours. Fifteen liters of this culture is then inoculated into 200 l of medium in a 300 l Chemap fermentor. Growth is at 30° C. until the $A_{590}$ reaches 3 (approximately 4 Hr), at 43° C. for 45 minutes, and then at 36° C. for 3.5 hr. Approximately 1.6 kg of cells are recovered and are stored at −70° C.

All purification steps are carried out at 4° C. The major deleterious contaminants in this enzyme are nucleases. To avoid introduction of nuclease contamination during practice of the invention, the following precautions are taken: Buffers are prepared in glassware which has been treated with 0.2 N NaOH, rinsed with distilled water, and baked at 120° C. to render them RNase free. Bottles used for the storage of buffers are treated in a similar fashion. All buffers are autoclaved in treated bottles and detergent and dithiothreitol added just prior to use. Columns, tubing, fittings, and glassware are treated with alkali as described and autoclaved when possible.

Five hundred grams of frozen *E. coli* 4830(RT601) cells are thawed at 4° C. until soft and then added to 5 liters of buffer A (25 mM Tris-HCl, pH 8, 25 mM KCl, 1 mM EDTA, and 1 mM dithiothreitol). The cells are dispersed by gentle mixing with a Turrax homogenizer. Five ml of a 0.1 M solution of phenylmethylsulfonyl fluoride (PMSF) prepared in anhydrous ethanol is added, and then 50 ml of a freshly prepared solution of lysozyme (13 mg/ml in 0.25 M Tris-HCl (pH 8.0) and 1 mM EDTA) is added. The suspension is left to sit for 20 minutes with occasional stirring. The viscous spheroplast suspension is rendered 0.2 mM PMSF by addition of 5 ml more of 0.1 M PMSF and then is lysed by the addition of 250 ml of a 10% (w/v) solution of sodium deoxycholate. The suspension increases in viscosity significantly after the addition of the detergent and is allowed to sit for 20 minutes to effect complete lysis.

To the viscous lysate is added 150 ml of 5 M NaCl followed by 500 ml of 5% (w/v) Polymin P (adjusted to pH 8.0). The Polymin P is added in aliquots of 5 to 10 ml over 2 to 3 minutes while the suspension is stirring. After all the Polymin P is added, the solution is stirred for an additional 20 minutes and then centrifuged at 8000 xg for 20 minutes.

To the clarified supernatant fluid is added 0.225 grams of crystalline $(NH_4)_2SO_4$ per ml of supernatant over a period of 30 minutes with constant, gentle stirring. After all of the salt is dissolved, the turbid solution is allowed to stir for an additional 30 minutes. The precipitate is collected by centrifugation at 8,000 xg for 20 minutes and the pellets are resuspended in 300 ml of buffer B (20 mM Tris-HCl (pH 7.5), 0.1 M NaCl, 1 mM EDTA, 1 mM dithiothreitol, 0.01% (w/v) N-octyl-$\beta$-D-glucopyranoside, and 5% (v/v) glycerol) by gentle manual homogenization. After stirring gently for 1 hour to aid dissolution of the pellet, the solution is clarified by centrifugation at 10,000×g for 10 minutes and desalted on a 2000 ml (5×100 cm) column of Sephacryl S-200 equilibrated with buffer B and eluted with the same buffer at 100 to 120 ml/hour. The excluded volume from the Sephacryl S-200 column is loaded immediately onto a 125 ml (2.5×25 cm) column of phosphocellulose equilibrated with buffer B. The column is washed with 250 ml of buffer C [20 mM Tris-HCl (pH 7.5), 1 mM EDTA, 1 mM dithiothreitol, 5% (v/v) glycerol, and 0.01% (v/v) NP-40]+0.1 M NaCl and developed with a 1000 ml linear gradient of buffer C+0.1 M NaCl to buffer C+0.5 M NaCl at a flow rate of 50 ml/hour. The RT elutes from the column in a sharp symmetrical peak at approximately 0.23 M NaCl.

The pooled peak of active enzyme from the phosphocellulose column is diluted to a NaCl concentration of 0.125 M by the addition of buffer C and loaded onto a 125 ml (2.5×25 cm) column of heparin agarose and washed with 100 ml of buffer C+0.1 M NaCl, at a flow rate of 50 to 70 ml/hour. The column is then washed with 4 liters of buffer C+0.24 M NaCl at a flow rate of 100 to 150 ml/hour. The RT is eluted with a 1000 ml linear gradient of buffer C+0.24 M NaCl to buffer C+1.0 M NaCl at a flow rate of 50 ml/hour. The RT elutes from the column coincident with the major $A_{280}$ absorption peak at about 0.38 M NaCl.

The pooled peak of active enzyme from the heparin column is dialyzed against storage buffer containing 20 mM Tris-HCl (pH 7.5), 1 mM dithiothreitol, 0.1 mM EDTA, 0.1 M NaCl, 0.01% NP-40, and 50% glycerol. The yield of nearly homogeneous RT protein is 70 to 80 mg.

We claim:

1. A plasmid carrying genetic material derived from murine leukemia virus, wherein said genetic material encodes a protein truncated three amino acids or more from the carboxy terminus of native murine leukemia virus reverse transcriptase, wherein said protein exhibits reverse transcriptase activity with a half-life of 26–35 minutes.

2. A plasmid carrying genetic material derived from murine leukemia virus, wherein said genetic material encodes a protein truncated three amino acids or more from the carboxy terminus of native murine leukemia virus reverse transcriptase, wherein said protein contains an $\alpha$-helix of 18 amino acids adjacent to the carboxy end of said protein.

3. A bacterial cell containing the plasmid of claim 1 or 2.

4. Plasmid pRT601.

5. *E. coli* strain N4830 containing plasmid pRT601.

* * * * *